United States Patent
Kim et al.

(10) Patent No.: US 9,962,331 B2
(45) Date of Patent: May 8, 2018

(54) COMPOSITION CONTAINING HORSE CHESTNUT EXTRACT

(75) Inventors: Min-Young Kim, Daejon (KR); Byung-Young Park, Daejon (KR); Chang-Hee Moon, Daejon (KR); Eun-Kyu Park, Daejon (KR); Kyoung-Mi Kim, Cheonju (KR)

(73) Assignee: Angiolab, Inc., Daejeon (KR)

( * ) Notice: Subject to any disclaimer, the term of this patent is extended or adjusted under 35 U.S.C. 154(b) by 0 days. days.

(21) Appl. No.: 10/832,713

(22) Filed: Apr. 26, 2004

(65) Prior Publication Data

US 2004/0234633 A1    Nov. 25, 2004

Related U.S. Application Data

(63) Continuation-in-part of application No. PCT/KR02/02000, filed on Oct. 25, 2002.

(30) Foreign Application Priority Data

Oct. 26, 2001 (KR) .................. 10-2001-0066246
Oct. 17, 2002 (KR) .................. 10-2002-0063407

(51) Int. Cl.
| | |
|---|---|
| *A61K 9/00* | (2006.01) |
| *A61K 9/20* | (2006.01) |
| *A61K 36/77* | (2006.01) |
| *A61K 47/02* | (2006.01) |
| *A61K 47/10* | (2017.01) |
| *A61K 47/12* | (2006.01) |
| *A61K 47/14* | (2017.01) |
| *A61K 47/42* | (2017.01) |

(52) U.S. Cl.
CPC .......... *A61K 9/0014* (2013.01); *A61K 9/0019* (2013.01); *A61K 9/2059* (2013.01); *A61K 36/77* (2013.01); *A61K 47/02* (2013.01); *A61K 47/10* (2013.01); *A61K 47/12* (2013.01); *A61K 47/14* (2013.01); *A61K 47/42* (2013.01)

(58) Field of Classification Search
USPC ................................ 424/725, 401
See application file for complete search history.

(56) References Cited

U.S. PATENT DOCUMENTS

| | | | | |
|---|---|---|---|---|
| 3,992,519 A | * | 11/1976 | Hofmann et al. | 424/48 |
| 4,486,404 A | * | 12/1984 | Weinert | 424/54 |
| 4,663,354 A | | 5/1987 | Neiderhauser et al. | |
| 5,043,153 A | * | 8/1991 | Videki et al. | 424/49 |
| 5,080,901 A | | 1/1992 | Hangay et al. | |

FOREIGN PATENT DOCUMENTS

| | | | |
|---|---|---|---|
| DE | 19653100 A1 | * | 7/1998 |
| EP | 0900563 A1 | | 3/1999 |
| JP | 62-81325 | | 4/1987 |
| JP | 07033632 A | * | 2/1995 |
| JP | 10-175842 | * | 6/1998 |
| JP | 11222419 A | * | 8/1999 |
| JP | 2000128753 A | * | 5/2000 |
| KR | 138248 B1 | * | 5/1998 |
| KR | 20000050855 A | * | 8/2000 |

OTHER PUBLICATIONS http://www.rain-tree.com/lemonbalm.htm—accessed Jul. 2008.*
Product Alert ((1999), vol. 29, No. 15).*
Translation of KR 138248—1998.*
Gernot Katzer's Spice Pages. "Lemon Balm (*Melissa officinalis* L.)". Dec. 17, 1999 Retrieved from the Internet on: Oct. 1, 2011. Retrieved from the Internet: <URL: http://www.uni-graz.at/~katzer/engl/Meli_off.html>.*
Loew et al., "Measurement of the bioavailability of aescin-containing extracts", Methods Find Exp Clin Pharmacol. 2000, 22(7): 537-542.
Matsuda et al., "Effects of escins Ia, Ib IIa, and IIb from horse chestnut, the seeds of *Aesculus hippocastanum* L., on acute inflammation in animals", Biol. Pharm. Bull. 1997 20(10): 1092-1095.
Ramamurthy NS, et al., "Inhibition of alveolar bone loss by matrix mellaproteinase inhibitors in experimental periodontal disease," J Periodont Res., 37:1-7, 2002.

* cited by examiner

*Primary Examiner* — Amy L Clark
(74) *Attorney, Agent, or Firm* — JHK Law; Joseph Hyosuk Kim

(57) ABSTRACT

The present invention relates to a composition containing Horse chestnut extract that inhibits angiogenesis and matrix metalloproteinase activity. The Horse chestnut extract of the present invention inhibits angiogenesis and activity of matrix metalloproteinase, so that it can be applied to treat and prevent disease related to angiogenesis and/or matrix metalloproteinase.

17 Claims, 14 Drawing Sheets

Fig. 13

| | Control | Horse chestnut | | DOXY | |
|---|---|---|---|---|---|
| | | 0.5% | 0.05% | 0.5% | 0.05% |
| MMP | -1  -13 | -1  -13 | -1  -13 | -1  -13 | -1  -13 |

Lane 1: Marker
Lane 2: PBS control
Lane 3: LPS control
Lane 4: treated with Horse chestnut extract and Melissa leaf extract

COMPOSITION CONTAINING HORSE CHESTNUT EXTRACT

CROSS-REFERENCE TO RELATED APPLICATIONS

The present application is a continuation-in-part application claiming benefit of priority to PCT/KR02/02000, filed on Oct. 25, 2002, the contents of which are incorporated by reference herein in its entirety.

BACKGROUND OF THE INVENTION

1. Field of the Invention

The present invention relates to a composition comprising Horse chestnut extract having anti-angiogenic and matrix metalloproteinase inhibitory activity for the prevention and treatment of diseases caused by abnormal angiogenesis and its use thereof.

2. General Background and State of the Art

Angiogenesis is the process of generating new capillary blood vessels. Neovascularization is tightly regulated, and activation occurs in embryogenic development, tissue remodeling, wound healing and periodic cycles of corpus luteum development (Folkman and Cotran; *Int. Rev. Exp. Pathol.*, 16, pp207-248, 1976).

Vasculogenesis means the formation of new endothelial cell during the embryogenesis in order to supply the nutrient for rapidly growing fetus. On the contrary, capillary blood vessel endothelial cells are started to proliferate from existing vasculature in angiogenesis. The endothelial cells are growing very slowly as compared with other types of cells in the body. However, the proliferation of these cells is induced by pro-angiogenic cytokines, inflammation mediators and activated proteolytic enzymes.

By the failure of regulation of angiogenesis, some pathological syndromes are developed (Timar; *J. Pathol. Oncol Res.*, 6, pp85-94, 2001). Pathological angiogenesis is involved in many diseases. For example, cardiovascular diseases such as angioma, angiofibroma, vascular deformity, atherosclerosis, synechia and edemic sclerosis; and opthalmological diseases such as neovascularization after cornea implantation, neovascular glaucoma, diabetic retinopathy, angiogenic corneal disease, macular degeneration, pterygium, retinal degeneration, retrolental fibroplasias, and granular conjunctivitis are diseases related to angiogenesis. Chronic inflammatory diseases such as arthritis; dermatological disease such as psoriasis, telangiectasis, pyogenic granuloma, seborrheic dermatitis and acne are also angiogenesis-dependent diseases.

In particular, angiogenesis is essential to metastasis and growth of cancer (D'Amato R J and Adamis A P, *Ophthalmol.*, 102, pp1261-1262, 1995; Arbiser J L, *J. Am. Acad. Derm.*, 34, pp486-497, 1996; O'Brien K. D. et al.; *Circulation*, 93, pp672-682, 1996; Hanahan D and Folkman J, *Cell*, 86, pp353-364, 1996). New blood vessels not only provide nutrients and oxygen to fast-growing cancer cells, but also give ways of entering the blood stream resulting metastasis (Polverini P. J., *Critical Reviews in Oral Biology*, 6, pp230-247, 1995). Currently, a large variety of chemotherapies and immunotherapies are applied in the treatment of cancer, but the efficacy of the therapies is limited and nothing can successfully extend the life of cancer patients due to the lack of anti-metastasis effects.

Arthritis, a well-known inflammatory disease, is initiated as an autoimmune disease. As the progression of the inflammation, the growth of vascular endothelial cell in the synovial cavity is activated by the cytokines. The cartilage in the articulation is finally destroyed by the formation of articular lamina leak (Kocb A E, et al., *Arth. Rheum.*, 29, pp471-479, 1986; Stupack D G, et al.; *Braz. J. Med. Biol. Rcs.*, 32, pp578-581, 1999; Koch A E; *Arthritis Rheum.*, 41, pp951-962, 1998).

Many people are losing their eyesight all over the world because of various ocular diseases. Many patients become blind due to the infiltration of the capillary blood cells into the vitreous humor (Jeffrey M I and Takayuki A, *J. Clin. Invest.*, 103, pp1231-1236, 1999). Therefore, inhibition of angiogenesis is the basic therapeutic modality for these diseases.

Psoriasis is caused by extremely active proliferation of skin cells. Fast-growing cells requires sufficient blood supply, and angiogenesis is abnormally induced in psoriasis (Folkman J., *J. Invest. Dermatol.*, 59, pp40-48, 1972).

Since angiogenesis is closely related to initiation and progression of many diseases, many efforts have been made toward the development of angiogenesis inhibitors in order to prevent and/or treat those diseases.

Not only reorganization of the blood vessel by migration, proliferation and differentiation of endothelial cells, but also degradation of the extracellular matrix is required for angiogenesis. One of the major events for inducing angiogenesis is a breakdown of the extracellular matrix before the formation of the capillary blood vessels. The most important enzyme of matrix degradation is matrix metalloproteinase (MMP), a family of over 20 proteins. MMPs are endopeptidase, which degrade or proteolyze the components of the extracellular matrix such as collagen, proteoglycan, and gelatin, and are classified into four groups: collagenase, gelatinase, stromelysin, and membrane-type MMP. Many enzymes in the MMP family have substrate specificity. The expression of MMP is induced under various physiological circumstances when remodeling of an extracellular matrix is required (Curry T E Jr., Osteen K G; *Biol. Reprod.*, 64, pp1285-1296, 2001; Damjanovske S, et al., *Ann. NY. Acad. Sci.*, 926, pp180-191, 2000; Ravanti L, Kahari V M, *Int. J. Mol. Med.*; 6, pp391-407, 2000).

Increased expression or activation of MMPs is observed in many pathological states, such as atherosclerosis, restenosis, MMP-dependent-osteopathy, inflammation of the central nervous system, Alzheimer's disease, skin aging, rheumatoid arthritis, osteoarthritis, septic arthritis, corneal ulcer, synechia, bone disease, proteinuria, abdominal aortic aneurysm, regressive cartilage loss, myelinated nerve loss, liver fibrosis, nephroglomerular disease, germinal membrane ruptures, inflammatory bowel disease, gingivitis, periodontitis, senile macular degeneration, diabetic retinopathy, proliferate vitreous body retinopathy, immature retinopathy, eye inflammation, conical cornea, Sjogren's syndrome, myopia, eyes tumors, rejection of cornea implantation, angiogenesis and cancer metastasis. (Woessner Jr., *Ann. NY. Acad. Sci.*, 732, pp11-21, 1994; Warner et al., *Am. J. Pathol.*, 158, pp2139-44, 2001; Stetler-Stevenson, *Surg. Oncol. Clin. N. Am.*, 10, pp383-92, 2001).

For example, stromelysins are known to be the major enzyme for disruption of cartilage (Murphy, G. et al., *Biochem. J.*, 248, pp265-268, 1987). Collagenases, gelatinases and stromelysins are responsible for the degradation of the extracellular matrix in many retinopathies (Bruns, F. R. et al., *Invest. Opthalmol. and Visual Sci.*, 32, pp1569-1575, 1989). Collagenases and stromelysins are identified in fibroblast from gingiva in inflammation, and the activity of the enzyme is dependent on the degree of inflammation (Overall, C. M. et al., *J Periodontal Res*, 22, pp81-88, 1987).

MMP activity is highly enhanced in response to the bacterial infection and inflammation in gingival crevicular fluid taken from patients with periodontal disease. Destruction of collagen, a major structural component of the periodontal matrix, by MMP leads to gingival recession, pocket formation and tooth movement (Goulb, L B., Ryan M. E. Williams R. C., *Dent. Today,* 17, pp102-109).

Recent reports have also shown that MMP-1 activity is highly induced in Alzheimer's disease, and MMP-1 and MMP-3 are involved in the pathophysiology of the disease (Leake A, et al.; *J. Neurosci. Lett.,* 291, pp201-3, 2000; Yoshiyama Y, et al., *Acta Neuropathol.* (Berl), 99, pp91-5, 2000).

MMPs are also responsible in solar UV radiation-induced skin damage, affecting skin tone and resiliency leading to premature aging. The symptom of that include leathery texture, wrinkles, mottled pigmentation, laxity and sallowness. Therefore, MMP inhibitors could be included in cosmetics for anti-photoaging or anti-wrinkle treatment (Hase T, et al., *Br. J. Dermatol.,* 142, pp267-273, 2000; Fisher G. J, et al.; *Photochem. Photobiol.,* 69, pp154-157, 1999).

Since inhibitors of MMP and angiogenesis can be applied to the treatment and prevention of many diseases, development of angiogenesis inhibitor as new therapeutics is expected. Since these inhibitors need to be administered for a long time, desirable inhibitors should not have toxic or adverse effect with good patient compliance.

Horse chestnut is a plant in Hippocastanaceae, cultivated in many countries in Europe and Asia. Triterpene saponin mixture known as aescin (also called escin) consists of diacylated tetra- and pentahydroxy-beta-amyrin compounds is a chief component of the seeds. Various flavonoids and polysaccharides are also included in the seeds. In addition to aescin, the leaves contain hydroxycoumarin such as esculin, fraxin and scopolin and flavonoids including rutin, quercitrin and isoquercitrin.

In folk medicine, the leaves have been used as a cough remedy. Japanese Horse chestnut seeds are given to patient with gastric pain, malaria, and diarrhea. Purified extract from Horse chestnut seed can be used for preparation of traditional Japanese cakes.

Horse chestnut seeds are used for treatment of symptoms in chronic venous insufficiency, because of anti-exudative and vascular tightening effects of the principal ingredient of seed extract, aescin.

Periodontal (gum) diseases, including gingivitis and periodontitis, are serious infections that, left untreated, can lead to tooth loss. Periodontal disease is a chronic bacterial infection that affects the gums and bone supporting the teeth. Periodontal disease may affect one tooth or many teeth. It begins when the bacteria in plaque causes the gums to become inflamed. In the mildest form of the disease, gingivitis, the gums redden, swell and bleed easily. Gingivitis is often caused by inadequate oral hygiene. Gingivitis is reversible with professional treatment.

Untreated gingivitis can advance to periodontitis. With time, plaque can spread and grow below the gum line. Toxins produced by the bacteria in plaque irritate the gums. The toxins stimulate a chronic inflammatory response, and the tissues and bone that support the teeth are broken down and destroyed. Gums separate from the teeth, forming spaces between the teeth and gums that become infected. As the disease progresses, the spaces deepen and more gum tissue and bone are destroyed. Eventually, teeth can become loose and may have to be removed.

Some of the main causes of periodontal disease is bacterial plaque. However, factors like the following also affect the health of the gums, such as smoking, genetics—up to 30% of the population may be genetically susceptible to gum disease. Stress is another cause.

The most common ones include the following. Gingivitis is the mildest form of periodontal disease. It causes the gums to become red, swollen, and bleed easily. There is usually little or no discomfort at this stage. Gingivitis is reversible with professional treatment and good at home oral care. Aggressive periodontitis is a form of periodontitis that occurs in patients who are otherwise clinically healthy. Common features include rapid attachment loss and bone destruction and familial aggregation. Chronic periodontitis is a form of periodontal disease resulting in inflammation within the supporting tissues of the teeth, progressive attachment and bone loss and is characterized by pocket formation and/or recession of the gingiva. It is recognized as the most frequently occurring form of periodontitis. It is prevalent in adults, but can occur at any age. Progression of attachment loss usually occurs slowly, but periods of rapid progression can occur. Also, periodontitis may be a manifestation of systemic diseases, such as diabetes. Necrotizing periodontal diseases is an infection characterized by necrosis of gingival tissues, periodontal ligament and alveolar bone. These lesions are most commonly observed in individuals with systemic conditions including, but not limited to, HIV infection, malnutrition and immunosuppression.

Periodental diseases may be treated by surgery such as pocket reduction, soft tissue grafts, regeneration procedures, crown lengthening.

The present inventors have studied the inhibitory effect of Horse chestnut extract on angiogenesis and matrix metalloproteinase and have discovered that the Horse chestnut extract could be used to inhibit a variety of angiogenesis- and MMP-dependent diseases, including early and late stage periodontal diseases.

SUMMARY OF THE INVENTION

The present invention is directed to a composition comprising a Horse chestnut extract for inhibiting angiogenesis. The composition may comprise a pharmaceutically acceptable carrier and may be used pharmaceutically, dermatologically, cosmetically, or topically. In a particular application of gum disease, the composition may be in solution or paste form so as to be in contact with gum. As a pharmaceutical composition it may be used for prevention and treatment of angiogenesis—dependent diseases. The extract may be made from *Aesculus turbinata* Blume, *Aesculus chinensis* Bge or *Aesculus wilculus* Rehd*Aesculus hippocastanum* L. Further, the extract may be made from leaves or seeds of *Aesculus turbinata* Blume, *Aesculus chinensis* Bge or *Aesculus wilculus* Rehd*Aesculus hippocastanum* L.

Horse chestnut extract used for inhibiting angiogenesis may be used to treat a variety of diseases including but not limited to cancer metastasis, angioma, angiofibroma, diabetic retinopathy, premature infant's retinopathy, neovascular glaucoma, corneal disease induced by angiogenesis, involutional macula, macular degeneration, pterygium, retinal degeneration, retrolental fibroplasias, granular conjunctivitis, psoriasis, telangiectasis, pyogenic granuloma, seborrheic dermatitis, acne, or arthritis.

The composition may be provided in a pharmaceutically acceptable carrier of tablet, capsule, soft capsule, aqueous medicine, syrup, elixirs, pill, powder, sachet, granule or injectable solution.

The composition may also be provided in a dermotologically acceptable carrier of a topical cream, lotion, ointment, gel, balm, spray, mouthwash, beverage or paste.

The invention is directed to a method of inhibiting angiogenesis-dependent disease comprising administering to a person in need thereof an effective amount of the composition. In this method, the disease to be treated may include without limitation cancer metastasis, angioma, angiofibroma, diabetic retinopathy, premature infant's retinopathy, neovascular glaucoma, corneal disease induced by angiogenesis, involutional macula, macular degeneration, pterygium, retinal degeneration, retrolental fibroplasias, granular conjunctivitis, psoriasis, telangiectasis, pyogenic granuloma, seborrheic dermatitis, acne, and arthritis.

The present invention is also directed to a composition comprising aescin, which is isolated from Horse chestnut extract for inhibiting angiogenesis. The present invention is also directed to a composition comprising esculetin or esculin purified from Horse chestnut extract for inhibiting angiogenesis. Further, the invention is directed to a composition comprising quercitrin purified from Horse chestnut extract for inhibiting angiogenesis.

In another aspect of the invention, the present invention is directed to a composition comprising a Horse chestnut extract for inhibiting matrix metalloproteinase activity. The composition may comprise a pharmaceutically acceptable carrier and may be used pharmaceutically, dermatologically, cosmetically, or topically, and in a particular application of gum disease, the composition may be in solution or paste form so as to be in contact with gum for prevention and treatment of matrix metalloproteinase-dependent diseases. The extract may be made from *Aesculus turbinata* Blume, *Aesculus chinensis* Bge or *Aesculus wilculus* Rehd*Aesculus hippocastanum* L. Further, the extract may be made from leaves or seeds of *Aesculus turbinata* Blume, *Aesculus chinensis* Bge or *Aesculus wilculus* Rehd*Aesculus hippocastanum* L.

The present invention is also directed to a pharmaceutical composition, which is used for prevention and treatment of without limitation at least one of disease selected from the group consisting of atherosclerosis, restenosis, MMP-dependent osteopathy, inflammation of central nervous system, Alzheimer's disease, skin aging, acne, rheumatoid arthritis, osteoarthritis, septic arthritis, corneal ulcer synechia, bone disease, proteinuria, abdominal aortic aneurysm, regressive cartilage loss, myelinated nerve loss, liver fibrosis, nephroglomerular disease, germinal membrane rupture, inflammatory bowel disease, gingivitis, periodontitis, senile macular degeneration, diabetic retinopathy, proliferate vitreous body retinopathy, immature retinopathy, eye inflammation, conical cornea, Sjogren's syndrome, myopia eye tumor, rejection of cornea implantation, angiogenesis, infiltration and cancer metastasis.

The pharmaceutical composition may further comprise a pharmaceutically acceptable carrier. The carrier may be in the form of without limitation a tablet, capsule, soft capsule, aqueous medicine, syrup, elixirs, pill, powder, sachet, granule or injectable solution. Further, the composition may be provided in a dermotologically acceptable carrier such as a topical cream, lotion, ointment, gel, balm, spray mouth wash, beverage or paste.

In another aspect of the invention, the invention is directed to a method of inhibiting MMP activity comprising administering to a person in need thereof an MMP inhibitory effective amount of the composition described above.

The invention is also directed to a method of controlling skin aging in a person comprising administering to the skin thereof a composition described above.

The invention is also directed to a method of treating gum inflammation in a person comprising administering an inflammation reducing effective amount of the composition described above. Such a composition may be in paste or solution form.

It is another object of the present invention to provide a mouth activity composition such as a beverage, mouth rinse, or toothpaste composition comprising Horse chestnut extract for prevention and treatment of gum inflammation or periodontal disease.

It is another object of the present invention to provide a use of the Horse chestnut extract for preparation of toothpaste composition for prevention and treatment of gum inflammation or periodontal disease.

It is another object of the present invention to provide a cosmetic composition for preventing skin aging comprising Horse chestnut extract having MMP-inhibitory activity or anti-angiogenesis activity.

It is another object of the present invention to provide a cosmetic composition comprising a Horse chestnut extract for preparation of cosmetic composition.

These and other objects of the invention will be more fully understood from the following description of the invention, the referenced drawings attached hereto and the claims appended hereto.

BRIEF DESCRIPTION OF THE DRAWINGS

The above and other objects and features of the present invention will become apparent from the following description of the invention, when taken in conjunction with the accompanying drawings, in which:

FIG. 13 is a picture showing inhibition of MMP-1 and -13 activities by Horse chestnut extract.

DETAILED DESCRIPTION OF THE PREFERRED EMBODIMENTS

Figure 1:
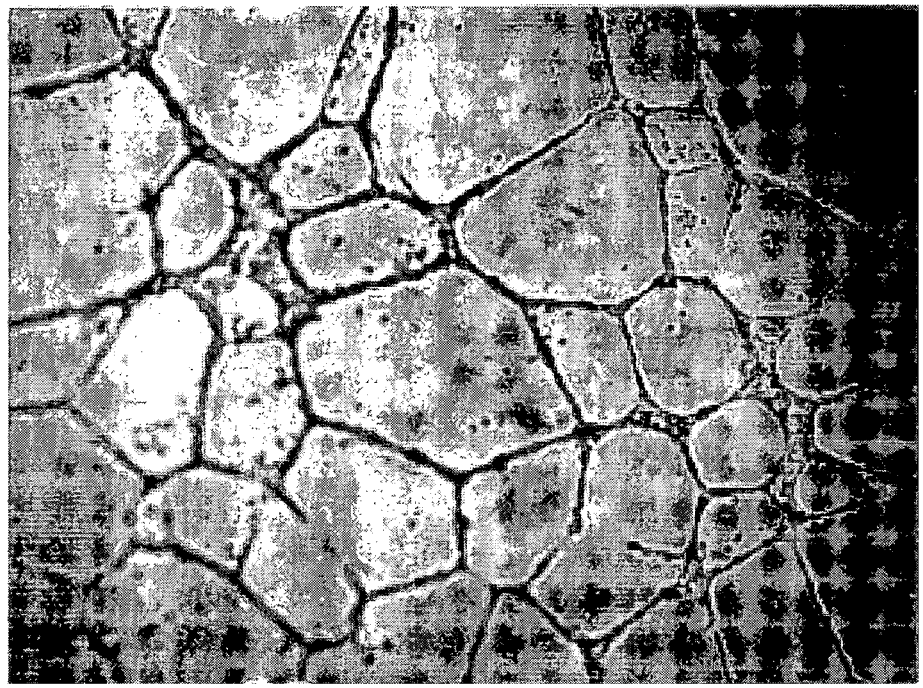
FIG. 1 is a picture showing tube formation of human umbilical vein endothelial cells (HUVEC) as a control.

In the present application, "a" and "an" are used to refer to both single and a plurality of objects.

Horse chestnut of the present invention comprise Japanese Horse chestnut (*Aesculus turbinata* Blume), Chinese (*Aesculus chinensis* Bge and *Aesculus wilculus* Rehd) and European (*Aesculus hippocastanum* L.) and the inventive extract is extracted from the leaves or the seeds from Japanese, Chinese or European Horse chestnut.

Horse chestnut extract of the present invention can be purchased or prepared with conventional methods. Commercially available Horse chestnut extract can also be used.

An inventive extract may be prepared in accordance with the following preferred embodiment.

For the present invention, Horse chestnut leaves are dried at room temperature and cut into small pieces. Quick dried-seeds at 30-40° C. or non-dried seeds are used and mashed or pulverized. The each powder is mixed with 3 to 10-fold, preferably, 5 to 7-fold volume of water, alcohols such as methanol, ethanol, butanol and the like, or the mixtures thereof, preferably, the mixture of water and methanol, more preferably 80% methanol; and is heated at a temperature ranging from 30 to 100° C., preferably from 50 to 80° C., for a period ranging from 1 to 48 hours preferably 3 to 10 hours, with 3 to 10 times, preferably 7 times, by sonication, reflux or conventional extraction to obtain an aqueous crude extract. The crude extract is centrifuged, filtered and then lyophilized to obtain an extract powder. The powder is stored at 4° C. until use.

In accordance with an aspect of the present invention, there is also provided a anti-angiogenic composition comprising Horse chestnut extract for inhibiting angiogenesis.

In accordance with another aspect of the present invention, there is also provided a pharmaceutical composition comprising Horse chestnut extract as an active ingredient for prevention and treatment of various diseases associated with angiogenesis.

Horse chestnut extract of the present invention inhibited angiogenesis not only in tube formation assay, but also in mouse Matrigel model when it was orally administered.

The tube formation assay is an in vitro experimental method that is closely related to in vivo efficacy, and this method investigates the microvascular network of the human endothelial cell. In vivo angiogenesis can be quantitatively measured in mouse Matrigel assay.

The extract of Horse chestnut inhibits MMP, a family of essential enzymes for angiogenesis and cancer metastasis. When the effect of Horse chestnut extract on MMPs was investigated with MMP-2 and MMP-13, it drastically inhibited activities of both enzymes. The inhibitory effect of Horse chestnut extract on MMPs is not, however, limited to these enzymes.

It is therefore clear that Horse chestnut extract of the present invention is available as a drug for angiogenesis- and/or MMP-dependent diseases since it inhibits angiogenesis and MMPs.

As mentioned above, Horse chestnut extract of the present invention has inhibitory effects on angiogenesis and MMP activity. While MMPs are enzymes responsible for angiogenesis, anti-angiogenic activity of Horse chestnut extract is not limited to MMP inhibition activity of the Horse chestnut. That is, MMPs are one of the factors for inducing angiogenesis, and Horse chestnut extract can inhibit other factors of angiogenesis. Furthermore, MMP inhibitory activity of Horse chestnut are not limited to inhibition of angiogenesis.

In accordance with another aspect of the present invention, there is also provided a composition comprising Horse chestnut extract having MMP-inhibitory activity.

In accordance with another aspect of the present invention, there is also provided a pharmaceutical composition comprising Horse chestnut extract as an active ingredient for prevention and treatment of various MMP-dependent diseases.

The inventive pharmaceutical composition can be used to prevent and treat angiogenesis- and/or MMP-dependent diseases, such as atherosclerosis, restenosis, MMP-dependent osteopathy, inflammation of central nervous system, Alzheimer's disease, skin aging, acne, rheumatoid arthritis, osteoarthritis, septic arthritis, corneal ulcer synechia, bone disease, proteinuria, abdominal aortic aneurysm, regressive cartilage loss, myelinated nerve loss, liver fibrosis, nephroglomerular disease, germinal membrane rupture, inflammatory bowel disease, gingivitis, periodontitis, senile macular degeneration, diabetic retinopathy, proliferate vitreous body retinopathy, immature retinopathy, eye inflammation, conical cornea, Sjogren's syndrome, myopia eye tumor, rejection of cornea implantation, angiogenesis, infiltration and cancer metastasis and so on.

The composition of this invention may be used by itself or included with more than one of other angiogenesis inhibitors, such as ticlopidine, glucosamine (2-amino-2-deoxy-D-glucopyranose) and *Ginkgo biloba* extract for the prevention and/or treatment of angiogenesis- and MMP-dependent diseases. We have previously reported that angiogenesis is inhibited by commercially available pharmaceutical composition comprising various extract and compounds such as Melissa leaf extract (KR10-2000-75488), glucosamine or its salt (KR-10-2001-18675), *Ginkgo biloba* extract (KR10-2000-45265) and ticlopidine (KR10-2000-43589).

The composition of the present invention comprising Horse chestnut extract may also comprise more than one component of other anti-cancer, anti-inflammatory and anti-aging agents such as *Glycyrrhiza glabra, Cinnamomum cassia, Sophora japonica, Atractylodes japonica, Atractylodes lancea, Artemisia capillaris, Morus alba, Houttuynia cordata, Lonicera japonica, Inula japonica, Inula britannica, Paeonia albiflora, Paeonia japonica, Paeonia obovata, Curcuma domestica, Curcuma longa, Saururus chinensis, Vaccinium myrtillus, Rubus* spp., *Melilotus officinalis, Angelica gigantis, Salvia officinalis, Salvia miltiorrhiza, Liriopeplatyphylla, Zingiber officinalis, Ulmus davidiana, Ulmus macrocarpa, Camellia japonica* and *Vitis vinifera*. Above compositions can be added to drugs, quasi-drugs, foods or beverages used for anti-angiogenic purpose.

The anti-angiogenic activity of above component is also confirmed by tube formation of HUVEC as previously mentioned.

The combined composition of horse chestnut with other anti-angiogenic agents could contain about 5-95 w/w %, most preferably 25-75 w/w % of horse chestnut of this invention out of total active ingredients.

Inventive pharmaceutical composition can be comprised in pharmaceutically acceptable diluent such as saline, buffered saline, dextrose, water, glycerol, ethanol and the mixture thereof, but it is not limited. Appropriate diluents are listed in the written text of Remington's Pharmaceutical Science (Mack Publishing co, Easton Pa.).

Accordingly, the present invention also provides a pharmaceutical composition for prevention and treatment of diseases caused by abnormal angiogenesis, which comprises the extract of Horse chestnut extract as an active ingredient, in combination with pharmaceutically acceptable excipients, carriers or diluents.

Examples of suitable carriers, excipients, and diluents are lactose, dextrose, sucrose, mannitol, starches, gum acacia, alginates, gelatin, calcium phosphate, calcium silicate, cellulose, methylcellulose, microcrystalline cellulose, polyvinylpyrrolidone, water, methylhydroxybenzoates, propylhydroxybenzoates, talc, magnesium stearate and mineral oil. The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a patient by employing any of the procedures well known in the art.

A formulation may be prepared by using the composition in accordance with any of the conventional procedures. In preparing the formulation, the active ingredient is preferably admixed or diluted with a carrier or enclosed within a carrier, which may be in the form of a capsule, sachet or other container. When the carrier serves as a diluent, it may be a solid, semi-solid or liquid material acting as a vehicle, excipient or medium for the active ingredient.

Pharmaceutical formulations containing Horse chestnut extract may be prepared in any form, such as oral dosage form (tablet, capsule, soft capsule, aqueous medicine, syrup, elixirs pill, powder, sachet, granule), or topical preparation (cream, ointment, lotion, gel, balm, patch, paste, spray solution, aerosol and the like), or injectable preparation (solution, suspension, emulsion).

The unit dosage of the formulation prepared above should contain 1 mg to 1000 mg, or preferably 5 to 500 mg of Horse chestnut extract in oral and injectable dosage forms. In general, 0.05 to 200 mg/kg of Horse chestnut extract can be administrated in a single dose or 2-3 divided doses per day. The composition may be composed of from about 0.01% to about 99% weight of horse chestnut extract. In particular, the amount may be without limitation about 0.1% to about 90%, about 5% to about 80%, about 5% to about 75%, about 5% to about 70%, about 5% to about 65%, about 5% to about 50%. For topical use, the amount may be without limitation from about 0.01% to about 99% weight, about 0.01% to about 90%, about 0.1% to about 80%, about 0.1% to about 75%, about 0.1% to about 50% and may be included in preparations such as emulsion, ointment, cream, spray and toothpaste.

In particular, 1 capsule may contain 250 mg of horse chestnut (Aesculus hippocastanum) seed extract powder standardized (20%) to supply 50 mg of aescin (triterpene glycosides). 1 capsule every 12 hours or as recommended by healthcare practitioner.

The pharmaceutical formulations comprising Horse chestnut extract of the present invention can be administered via various routes including oral, transdermal, subcutaneous, intravenous, intraperitoneal, intramuscular, intra-arterial, rectal, nasal, ocular, and topical introduction.

Horse chestnut extract composition may be applied differently according to the purpose of dosing and diseases. It should be understood that the amount of active ingredient has to be determined with various factors. These factors include the severity of the patient's symptoms, other co-administrated drugs (e.g., chemotherapeutic agents), age, sex, body weight of the individual patient, food, dosing time, the chosen route of administration, and the ratio of the composition.

In accordance with another aspect of the present invention, there is also provided a toothpaste composition comprising Horse chestnut having MMP-inhibitory activity for prevention and treatment of MMP-dependent diseases such as gingivitis and periodontitis.

The toothpaste composition contains an abrasive cleaning agent, a humectant, a binder and a flavoring agent and Horse chestnut extract.

It is preferable that the present toothpaste composition contains about 0.01 to about 99% by the weight of the Horse chestnut extract based on the total weight of the composition. The other components may be a mixture of the gradients of a conventional toothpaste composition.

For example, a humectant is at least one or two substance selected from the group consisting of glycerine, sorbitol solution and amorphous sorbitol solution. An abrasive cleaning agent is calcium hydrogen phosphate, calcium carbonate, aluminum oxide, and the like. Additives used in a small content are ordinary components used in the tooth paste and include sweetening agents, pH controlling agents, antiseptic substance, coloring agents and binders.

The sweetening agents are sodium saccharide, aspartame and the like, the pH controlling agents are sodium phosphate, disodium phosphate, citric acid and the like., and the antiseptic substances are paraoxy benzoin methyl, sodium benzoin and the like.

The binders or thickeners are sodium carboxymethyl cellulose, carrageenan, xantan gum, etc. A foaming agent may be anionic and non-ionic surfactants of sodium lauryl sulfate, saccharose carboxylic ester and sorbitan carboxylic ester in a sole form or in a combination of at least two thereof.

A flavoring agent is a mixture of peppermint oil, spearmint oil, menthol, etc., and other additives are enzyme such as dextranase, etc.

And the present invention to provide a use of the Horse chestnut extract for preparation of toothpaste composition to prevent and treat MMP-dependent diseases such as gingivitis and periodontitis.

In accordance with another aspect of the present invention, there is also provided a cosmetic composition for skin firmness comprising Horse chestnut having MMP-inhibitory activity.

It is preferable that the present cosmetic composition contains about 0.01 to about 99% by the weight of the Horse chestnut extract based on the total weight of the composition. The other components may be a mixture of the gradients of a conventional cosmetic composition known in the art.

Cosmetic formulations containing Horse chestnut extract may be prepared in any form such as cream, lotion, skin, gel, balm, spray solution and the like.

Furthermore, the present invention provides a use of the Horse chestnut extract for preparation of cosmetic composition for preventing skin aging.

Therefore, the above dose should not be intended to further illustrate the present invention without limiting its scope.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

The following examples are intended to further illustrate the present invention. However, these examples are shown only for better understanding the present invention without limiting its scope.

Example 1

Preparation of Extract from Horse Chestnut Leaf and Seed

Dried Horse chestnut leaves (500 g) or seeds (200 g) were crushed by blender and soaked in 2 L of 80% methanol. The solution was kept at 50° C. for 12 hrs and further extracted by sonication. The filtrate was concentrated by vacuum evaporator. Finally, 120 g of the extract from leaves and 53 g of the extract from seeds were obtained and used in the following examples.

Example 2

Identification of the Constituents of the Horse Chestnut Extract

Crude extract of Horse chestnut of the above EXAMPLE 1 was suspended in distilled water and extracted with 1 L of ethylacetate. After drying and solubilization in ethanol, an aliquot of the extract was subjected to paper chromatogrphy (BuOH:HAc:$H_2O$=4:1:5 vs. 2% ethylacetate)

From $R_f$ values with the standard compounds, the four main spots of the extract were identified as aescin, quercitrin, esculin and esculetin, respectively.

Experimental Example 1

Effect of Horse Chestnut Extract on Tube Formation of HUVEC

The effect of Horse chestnut extract on angiogenesis was investigated in vitro with human endothelial cells.

In order to do the tube formation assay, blood vessel endothelial cells, human umbilical vein endothelial cells (HUVECs), were isolated from freshly obtained cords after cesarean section according to Grant's method (Grants D S, et al., Cell, 58, pp933-943, 1989). They were identified by immunocytochemial staining with anti-Factor VIII antibody. HUVECs grown with Matrigel (BD Bioscience, Bedford, Mass., USA), were treated with the above Horse chestnut extract of the Example 1, and further incubated at 37° C. for 8-16 hrs. As a control, above procedure was repeated without Horse chestnut extract.

FIG. 1 shows that a tubular network is formed as a process of neovascularization, when they are grown on Matrigel.

Figure 2:
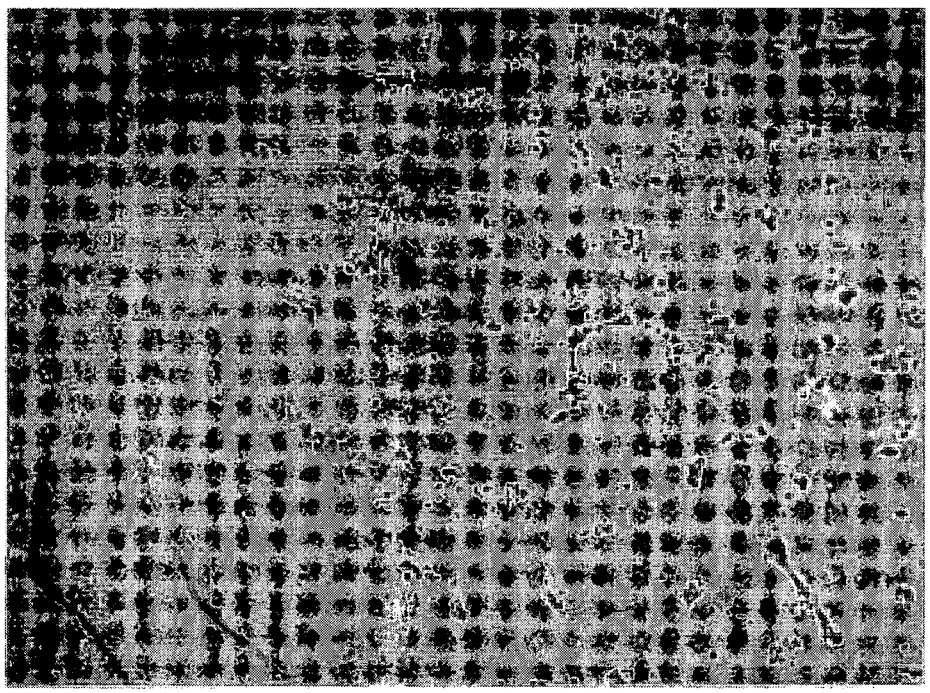
FIG. 2 is a picture showing HUVEC treated with 100 μg/Ml of European Horse chestnut extract.
Figure 3:
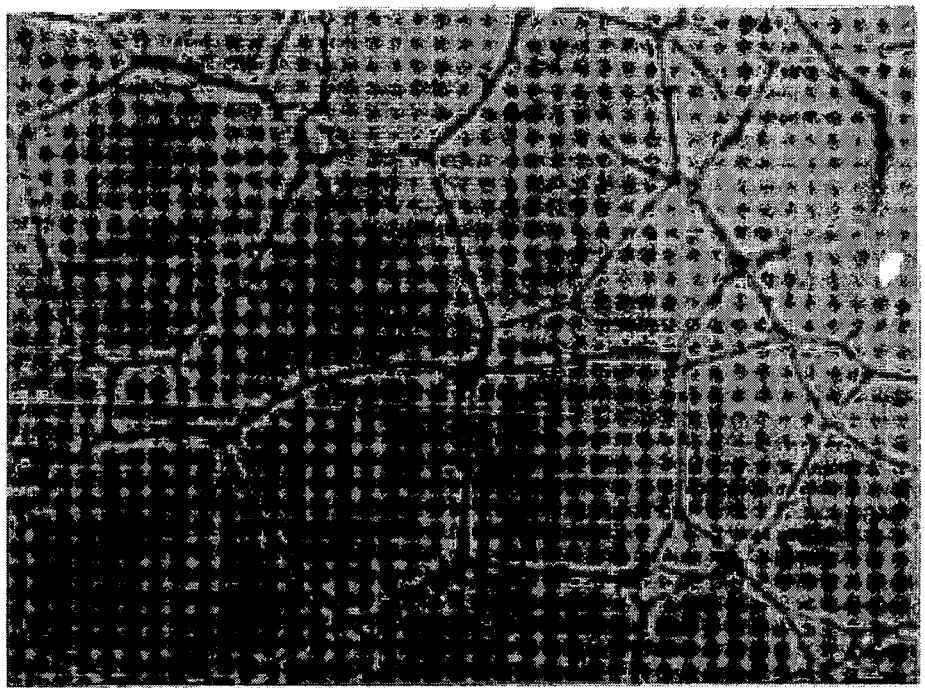
FIG. 3 is a picture showing HUVEC treated with 10 μg/Ml of Horse chestnut extract.
Figure 4:
FIG. 4 is a picture showing HUVEC treated with 100 μg/Ml of Japanese Horse chestnut extract.

FIGS. 2, 3 and 4 are pictures showing that the HUVECs grown on Matrigel treated with Horse chestnut extract cannot generate the microvascular network.

Figure 5:
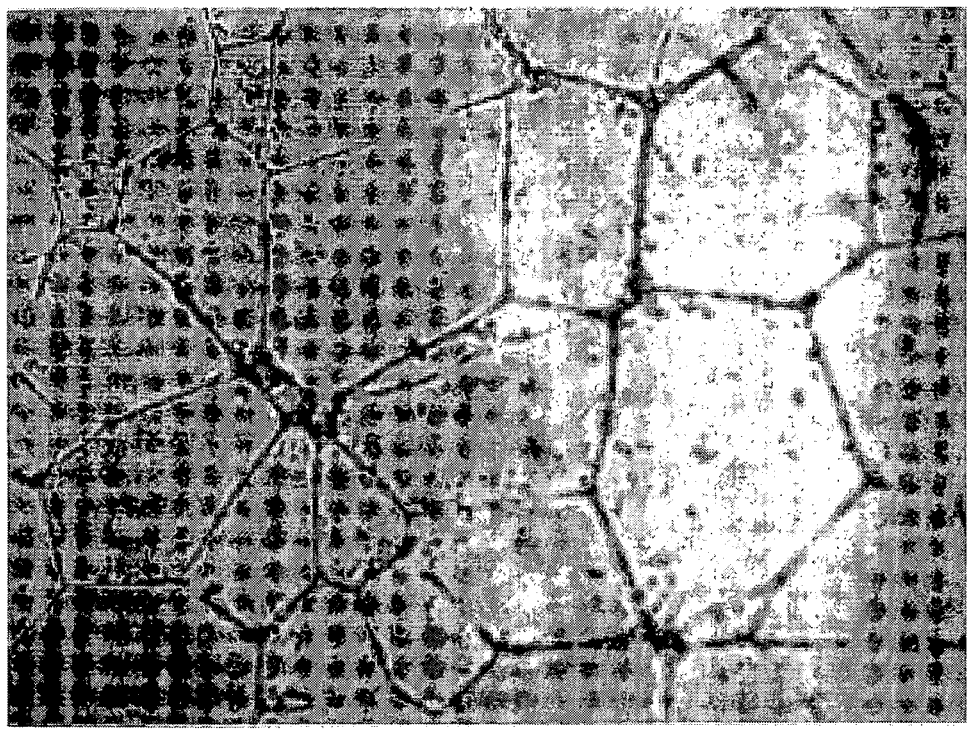
FIG. 5 is a picture showing HUVEC treated with DMSO.
Figure 6:
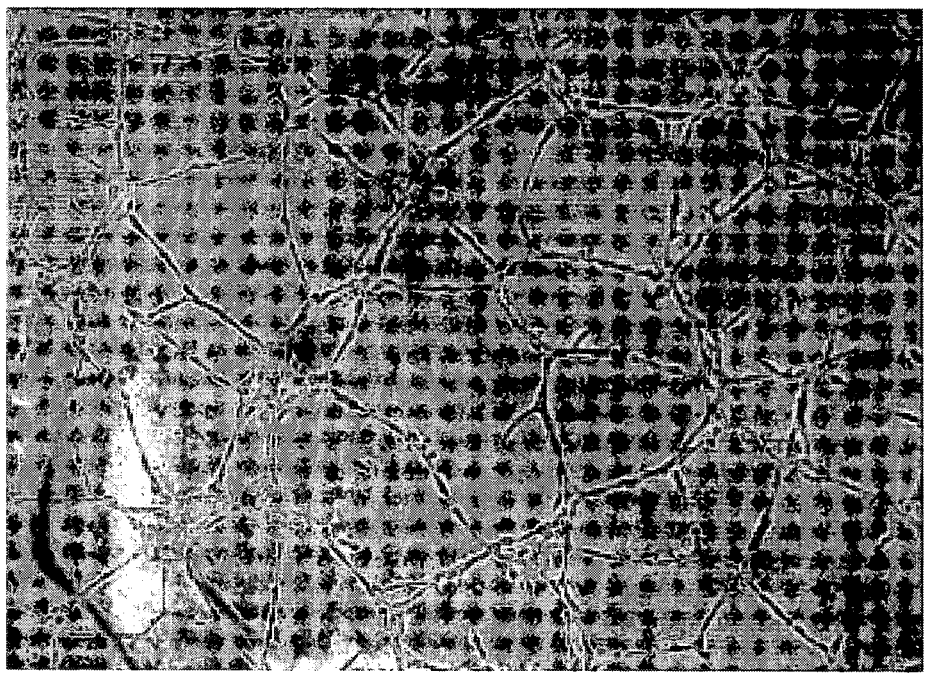
FIG. 6 is a picture showing HUVEC treated with 50 μM of esculin.
Figure 7:
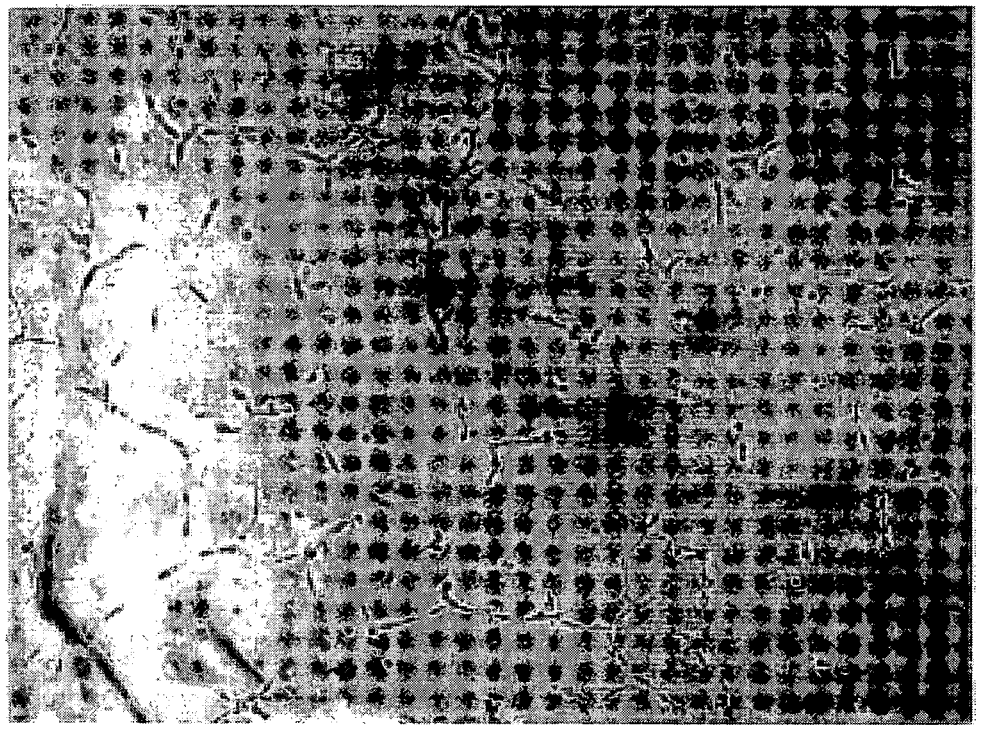
FIG. 7 is a picture showing HUVEC treated with 50 μM of esculetin.
Figure 8:
FIG. 8 is a picture showing HUVEC treated with 50 μM of quercitrin.
Figure 9:
FIG. 9 is a picture showing HUVEC treated with 50 μM of aescin.

In order to identify the component responsible for anti-aniogenic acvity of Horse chestnut extract, components identified as in EXAMPLE 2, were subjected to the tube formation assay as described above. Since those chemicals are not soluble in water, they were dissolved in dimethyl sulfoxide (DMSO). In order to exclude the effect of solvent, HUVECs treated with the same amount of DMSO were used as a control. FIG. 5 is a picture of the 1% DMSO-treated HUVEC control, and FIGS. 6-9 are pictures showing the effect of individual components of the Horse chestnut on tube formation. At 50 µM concentration, aescin completely inhibited the formation of microvascular network of HUVEC. Tubular network was disconnected by treatment with 50 µM of quercitrin, and esculetin. The extent of inhibition of tube formation by esculin was less than that by esculetin, aglycon of the esculin.

The area of the tube was determined by image analysis program Image-Pro Plus® (Media Cybernetics, USA), and the results were summarized in Tables 1 and 2. As shown in Table 1, Horse chestnut extract inhibited HUVEC tube formation in a dose-dependent manner.

TABLE 1

| Sample | Tube area | Percent Inhibition |
|---|---|---|
| Control | 10.55 | 0 |
| Horse chestnut extract (100 µg/Ml) | 0 | 100 |
| Horse chestnut extract (10 µg/Ml)MlMl | 8.89 | 16 |

TABLE 2

| Sample | Area of the Tube (%) | Percent Inhibition |
|---|---|---|
| Control | 100 | 0 |
| Esculin | 85 | 15 |
| Esculetin | 17 | 83 |
| Quercitrin | 36 | 64 |
| Aescin | 0 | 100 |

Experimental Example 2

Animal Experiment for Angiogenesis (Mouse Matrigel Model)

The anti-angiogenic activity of Horse chestnut extract was quantitatively measured in mouse Matrigel model.

0.4 Ml portion of Matrigel mixed with 50 ng/Ml of basic fibroblast growth factor (bFGF) and 50 units/Ml of heparin was implanted into C57BL/6 female mice of 6 to 8 week old (Daehan Biolink Co., Ltd., Korea) by subcutaneous injection. To each mouse, 1.0 mg of Horse chestnut extract of the Example 1 was orally administered twice a day for four days. After five days, the Matrigel was recovered from excised skin of each mouse and the amount of hemoglobin (Hb) in the Matrigel was measured by Drabkin kit(Sigma Chemical Co., St. Louise, Mich., USA, Cat. No. 525), a reagent for determination of total hemoglobin in blood.

Figure 10:
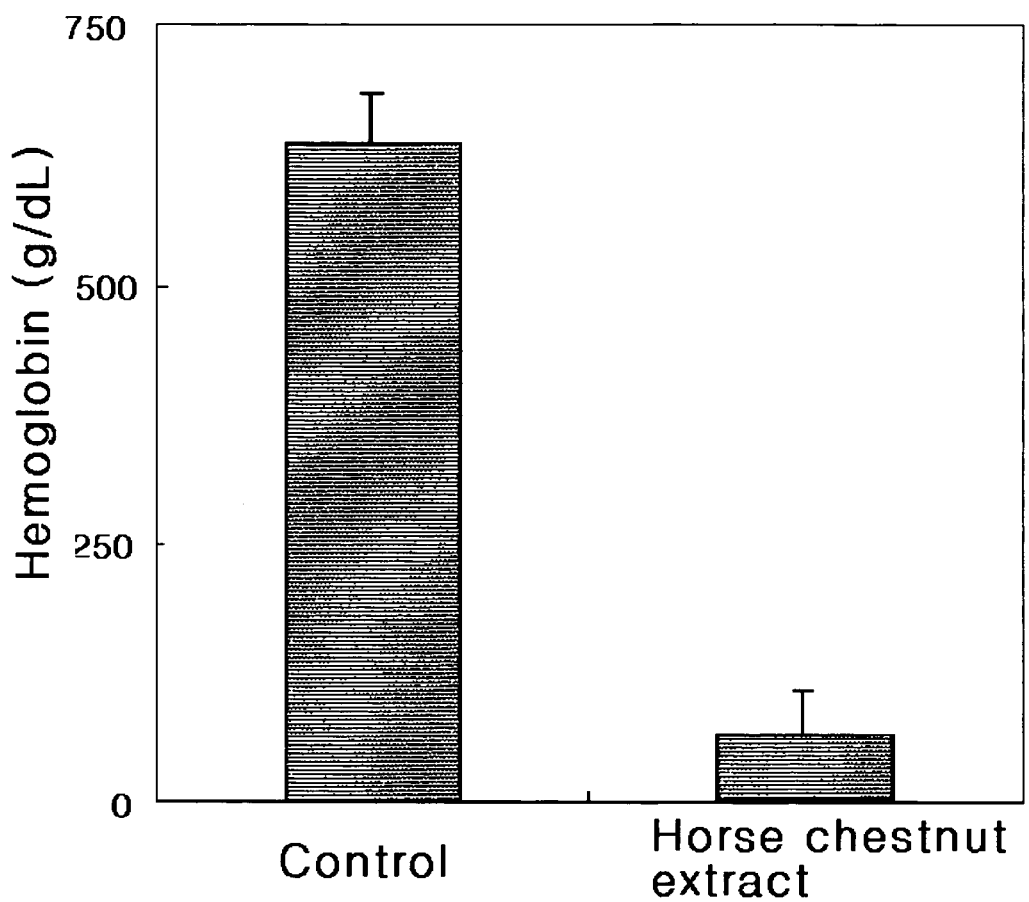
FIG. 10 is a graph showing the inhibition of angiogenesis by oral administration of Horse chestnut extract in the mouse Matrigel model.

As shown in FIG. 10 and Table 3, the average of total hemoglobin levels in the Matrigel from Horse chestnut extract-treated group were about 9.8% of that of the control group. That is, Horse chestnut extract potently inhibited growth factor induced angiogenesis by about 90% when it was administered orally.

TABLE 3

| | Hemoglobin (g/dL) |
|---|---|
| Control | 635 ± 50 |
| Horse chestnut extract | 62 ± 43 |

Experimental Example 3

Effect of other Anti-Angiogenic Extract on Tube Formation of HUVEC

The anti-angiogenic activity of *Atractylodes japonica* extract, *Artemisia capillaris* extract, *Vaccinium myrtillus* extract, *Houttuynia cordata* extract, and *Paeonia japonica* extract were also confirmed by tube formation of HUVEC experiment prosecuted by the procedure according to above Experimental Example 1. The inhibition of tube formation by 50 μg/Ml of each composition was 30-60% as compared with non-treated control HUVEC. Percent inhibition by 50 μg/Ml of crude extract show 52% for *Atractylodes japonica,* 53% for *Artemisia capillaris,* 40% for *Vaccinium myrtillus,* 30% for *Houttuynia cordata,* and 38% for *Paeonia japonica.*

TABLE 4

|  | Area of the Tube (%) | Percent Inhibition |
|---|---|---|
| Control | 100 | 0 |
| Atractylodes japonica | 48 | 52 |
| Artemisia capillaris | 47 | 53 |
| Houttuynia cordata | 70 | 30 |
| Vaccimium myrtillus | 60 | 40 |
| Paeonia japonica | 62 | 38 |

Experimental Example 4

Effect of Horse Chestnut Extract on Matrix Metalloproteinase Activity (1) Preparation of MMP MMP-2 and MMP-13 were cloned and prepared from insect cells (Sf21 insect cell) by using a Baculovirus system.

MMP-2 cDNA (GENBANK No. XM_048244) was cloned to a pBlueBac4.5 transfer vector (Invitrogen, Cat No. V1995-20), and then transfected to Sf9 cells with a Bac-N-Blue Transfection Kit (Invitrogen, Cat No. K855-01). Sf21 cells were incubated with a TNM-FH (Sigma Co, St. Louis, Mo., U.S.A) media containing 10% fetal bovine serum at 27° C., then harvested and re-suspended at a concentration of $10^7$ cell/Me. The cell suspension was incubated with a virus containing the cloned gene for 1 hr at room temperature. Infected Sf21 cells were grown for 72 hrs and the medium was recovered, and the MMP-2 was purified with a gelatin-sepharose affinity column from the recovered medium.

MMP-13 (GENBANK NO. XM_002427) was prepared from the corresponding genes as previously described, and purified with SP-sepharose chromatography.

(2) Inhibition of MMP Activity

In order to investigate MMP inhibition by Horse chestnut extract, MMP enzyme activity was assayed by a spectrofluorometric method (Perkin-Elmer LS50B).

Purified MMP-2 and MMP-13 were used after activation with 1 mM APMA before assay.

The substrate for MMP-2 was MCA-Pro-Leu-Gly-Leu-Dap(Dnp)-Ala-Arg-$NH_2$ (BACHEM, Cat. No. M-1895), and MCA-Pro-Cha-Gly-Nva-His-Ala-Dpa-$NH_2$ was used as a substrate for MMP-13.

As a control, 10 nM MMP-2 and 10 μM MMP-2 substrate were mixed in 2 Ml of reaction buffer (50 mM Tricine (pH 7.5), 10 mM $CaCl_2$, 200 mM NaCl) in a 2 Ml cuvette. Fluorescence intensity was measured for 5-10 min at room temperature with a spectrofluorometer under an excitation wavelength of 325 nm and an emission wavelength of 393 nm.

Horse chestnut extract (25 μg/Ml) dissolved in water and 10 nM MMP-2 were added to a reaction buffer containing a substrate, and fluorescence intensity was measured in the same manner.

Activity for MMP-13 was also assayed, and fluorescence intensity was measured as previously mentioned.

Figure 11:
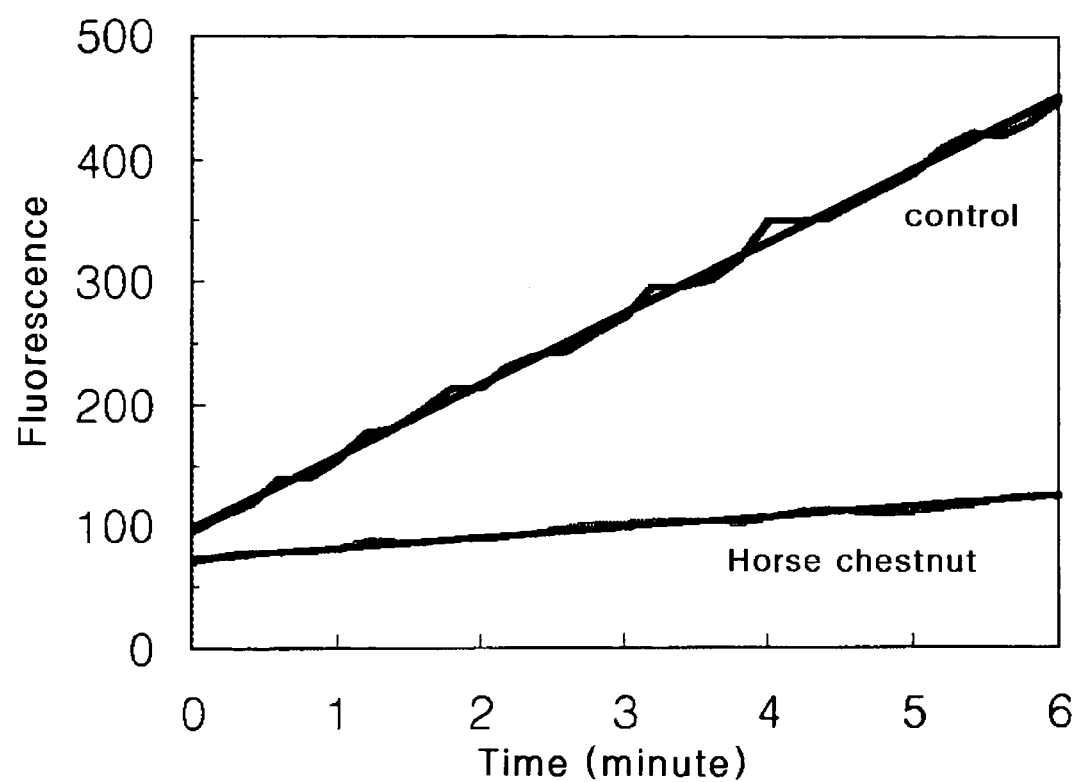
FIG. 11 is a graph showing inhibition of MMP-2 activity by Horse chestnut extract.
Figure 12:
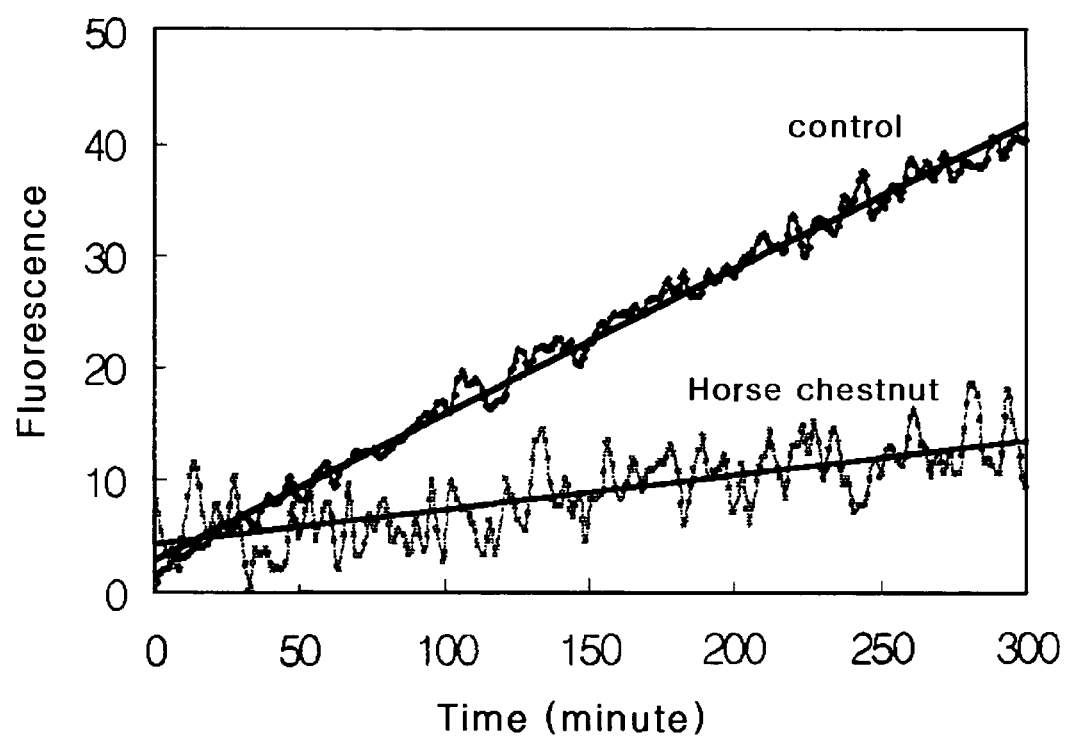
FIG. 12 is a graph showing inhibition of MMP-13 activity by Horse chestnut extract.

FIGS. 11 and 12 are diagrams of activity of MMP-2, and MMP-13. The inhibition of MMP-2 and MMP-13 by Horse chestnut extract was 77% (FIG. 11) and 85% (FIG. 12), respectively.

As mentioned previously, Horse chestnut extract of the present invention inhibits angiogenesis and matrix metalloproteinase activity. Based on such results, Horse chestnut extract can be used for prevention and treatment of angiogenesis- and/or MMP-dependent diseases.

Experimental Example 5

Inhibition of MMP-1 and -13 Activities by Horse Chestnut Extract in periodontal tissue The activities of matrix metalloproteinases (MMP) such as MMP-1, -13, -9 in the periodontal tissue is highly induced in periodontitis as a response to persistent bacterial infection, which is the most common cause of adult tooth loss. Collagenases (MMP-1, -8, -13) play major role in destruction of type I collagen matrix of periodontal ligaments and alveolar bone, that results in deeper pockets and bone loss.

Therefore, MMP inhibitors may be applied for periodontal disease to stop further damage and progression of the disease by blocking the breakdown of tissue and bone.

The inhibitory activity of Horse chestnut extract was compared with doxycycline, well-known commercial MMP inhibitor in casein zymogram. As shown in FIG. 13 the inhibitory effect of Horse chestnut extract on MMP-1 and MMP-13 activities is similar or greater than that of doxycycline.

Experimental Periodontitis was induced in adult male Sprague-Dawley rats (350-370 g) by injecting LPS endotoxin(Sigma Chemical). Under anesthesia each rat received three injections given every other day at 3 injection sites per animal. Injections were made into the anterior maxillary labial and palatal incisor gingivae. For control groups gingiva were injected with PBS or LPS and each rat was orally administered with vehicle, saline alone. For treatment group gingiva were injected with LPS and each rat was orally administered with 12.5 mg/kg of Horse chestnut extract and 12.5 mg/kg of Melissa leaf extract in saline daily. It is understood that the amount of Horse chestnut extract used may vary according to the individual subject, and therefore, the invention is not limited to the amount exemplified herein. The amount used may be from about 2 to about 50 mg/kg.

Figure 14:
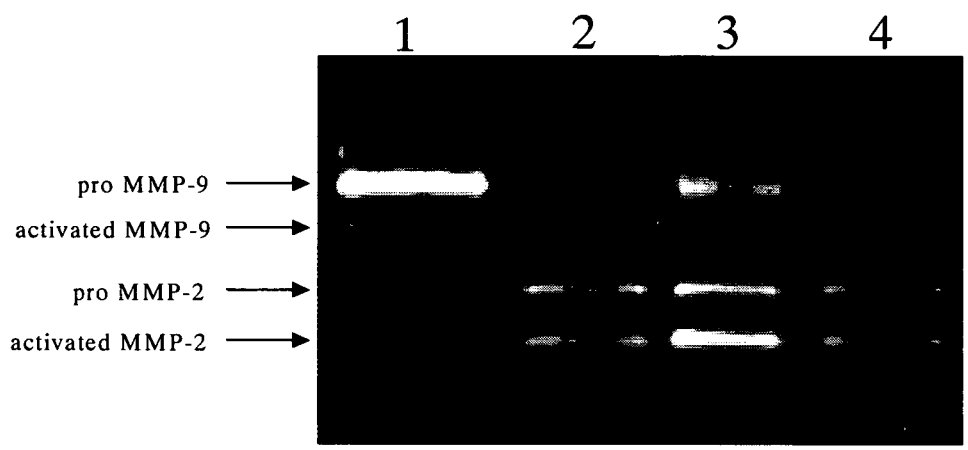
FIG. 14 is a picture showing gelatin zymogram of gingival tissue extract of rat periodontitis model.

On day 7, after euthanasia the gingival tissues from the anterior maxillary labial and palatal incisor gingivae were removed to measure the MMP activity. 100 mg of the gingival tissues were extracted with 5 ml of 5M urea buffer at 4° C. and the extract was concentrated with Amicon Ultra centrifugal filter (MW cut off 10,000, Millipore) for gelatin zymogram analysis. As shown in FIG. 14, oral administration of both Horse chestnut extract and Melissa leaf extract reduced proMMP-9, proMMP-2 and activated MMP-2 that were highly increased in LPS-induced periodontitis gingivae. The total MMP activities were decreased by oral administration of Horse chestnut extract and Melissa leaf extract. Therefore, the composition containing Horse chestnut extract can be administered orally to patients or can be included in mouth wash or tooth paste to treat or prevent periodontal disease.

Preparation Example 1

Preparation of Syrup

In this invention, syrup containing 2% Horse chestnut extract can be prepared as follows;

Dried powder of Horse chestnut extract, saccharin, glucose was dissolved in 80 g of warm water. After cooling, other ingredients were added thereto a volume of 100 Ml.

| | |
|---|---|
| Dried powder of Horse chestnut extract | 2.0 g |
| Saccharin | 0.8 g |
| Glucose | 25.4 g |
| Glycerin | 8.0 g |
| Fragrant | 0.04 g |
| Ethanol | 4.0 g |
| Sorbic acid | 0.4 g |
| Distilled water | q.s. |

Preparation Example 2

Preparation of Tablet

A tablet containing Horse chestnut extract was prepared with the following ingredients by mixing dried powder of Horse chestnut extract with lactose, starch and silica. Solution of 10% gelatin was added thereto, and the mixture was granulated by passing through the 14 mesh pharmaceutical sieve. After drying, granules were mixed with remaining ingredients and tableting was performed.

| | |
|---|---|
| Dried powder of Horse chestnut extract | 25.0 g |
| Lactose | 17.5 g |
| Starch | 34.0 g |
| Colloidal silica | 3.2 g |
| Talc | 5.0 g |
| Magnesium Stearate | 0.5 g |
| 10% gelatin | 10 Ml |

Preparation Example 3

Preparation of Injectable Solution

Horse chestnut extract, sodium chloride and ascorbic acid were dissolved in distilled water. When it dissolved completely, adequate amount of water was added thereto, to make the solution 100 Ml. The solution was sterilized as conventional method.

| | |
|---|---|
| Dried powder of Horse chestnut extract | 1.0 g |
| Sodium chloride | 0.6 g |
| Ascorbic acid | 0.1 g |
| Distilled water | q.s. |

Preparation Example 4

Preparation of Ointment

Horse chestnut extract, diethyl sebacate, polyoxyethylene and sodium benzoic acid were mixed in vaseline completely. And then adequate amount of Vaseline was added thereto, to make the mixture 100 g.

| | |
|---|---|
| Dried powder of Horse chestnut extract | 5.0 g |
| Diethyl sebacate | 8 g |
| Polyoxyethylene | 6 g |
| Sodium benzoic acid | q.s. |
| Vaseline | q.s. |

Preparation Example 5

Preparation of Toothpaste

Horse chestnut extract with the component listed in below were mixed in water completely. And then adequate amount of water was added thereto, to make the mixture 100 g.

| | |
|---|---|
| Dried powder of Horse chestnut extract | 5.0 g |
| Calcium Hydrogen Phosphate | 40 g |
| Amorphous Sorbitol | 25 g |
| Sodium Alkyl Sulfate | 2 g |
| Sodium Saccharide | 0.1 g |
| Carboxyl Methyl Cellulose | 1 g |
| Peppermint Oil | 0.8 g |
| Water | q.s. |

Preparation Example 6

Preparation of Lotion

Horse chestnut extract with the component listed in below were mixed in water completely. And then adequate amount of water was added thereto, to make the mixture 100 g.

| | |
|---|---|
| Dried powder of Horse chestnut extract | 5.0 g |
| L-ascorbic acid-2-magnesium phosphate | 1.0 g |
| Collagen | 1.0 g |
| Citric acid | 0.05 g |
| Sodium citrate | 0.1 g |
| 1,3-butyl glycerol | 3.0 g |
| Water | q.s. |

INDUSTRIAL APPLICABILITY

As above mentioned, Horse chestnut extract of the present invention inhibits angiogenesis and matrix metalloproteinase activity.

Based on the results, Horse chestnut extract can be used as a new composition for prevention and treatment of angiogenesis- and/or MMP-dependent diseases.

All of the references cited herein are incorporated by reference in their entirety.

Those skilled in the art will recognize, or be able to ascertain using no more than routine experimentation, many equivalents to the specific embodiments of the invention specifically described herein. Such equivalents are intended to be encompassed in the scope of the claims.

What is claimed is:

1. A method of treating early and late stage periodontal disease in a person in need thereof, said method comprising administering a composition consisting essentially of from 0.05 to 200 mg/kg/day of Horse chestnut leaf extract to the person.

2. The method according to claim 1, wherein the composition is in paste or solution form.

3. The method according to claim 1, wherein the composition is in gel, spray, mouth wash, toothpaste, beverage, tablet, capsule, soft capsule, aqueous medicine, syrup, elixir, pill, powder, sachet, ointment, granule or injectable solution form.

4. The method according to claim 1, wherein the composition further comprises a Melissa leaf extract.

5. The method according to claim 4, wherein the composition comprises from about 0.1% to about 90% by weight of Horse chestnut leaf extract and Melissa leaf extract.

6. The method according to claim 1, wherein the composition comprises from about 0.1% to about 90% by weight of Horse chestnut leaf extract.

7. The method according to claim 4, wherein the composition is in paste or solution form.

8. The method according to claim 4, wherein the composition is in gel, spray, mouth wash, toothpaste, beverage, tablet, capsule, soft capsule, aqueous medicine, syrup, elixir, pill, powder, sachet, ointment, granule or injectable solution form.

9. The method according to claim 1, wherein breakdown of gum tissue is blocked.

10. The method according to claim 1, wherein breakdown of bone is blocked.

11. The method according to claim 4, wherein the composition comprises from about 0.1% to about 90% by weight of Horse chestnut extract.

12. The method according to claim 4, wherein the composition is in paste or solution form.

13. The method according to claim 4, wherein the composition is in gel, spray, mouth wash, toothpaste, beverage, tablet, capsule, soft capsule, aqueous medicine, syrup, elixir, pill, powder, sachet, ointment, granule or injectable solution form.

14. The method according to claim 4, wherein the breakdown of gum tissue is blocked.

15. The method according to claim 4, wherein the breakdown of bone is blocked.

16. A method of treating early and late stage periodontal disease in a person in need thereof, said method comprising administering to said person a composition consisting essentially of from 0.05 to 200 mg/kg/day of Horse chestnut leaf extract to block breakdown of gum tissue or bone, wherein said Horse chestnut leaf extract is administered in an amount effective to inhibit matrix metalloproteinase in said person.

17. The method according to claim 16, wherein the matrix metalloproteinase is MMP-1, MMP-9 or MMP-13.

* * * * *